United States Patent [19]

Bloch et al.

[11] Patent Number: 5,565,339

[45] Date of Patent: *Oct. 15, 1996

[54] COMPOSITIONS AND METHODS FOR INHIBITING DIMERIZATION OF PRIMERS DURING STORAGE OF POLYMERASE CHAIN REACTION REAGENTS

[75] Inventors: Will Bloch, San Mateo; Jonathan C. Raymond, Orinda; Alan R. Read, Belmont, all of Calif.

[73] Assignee: Hoffmann-La Roche Inc., Nutley, N.J.

[*] Notice: The term of this patent shall not extend beyond the expiration date of Pat. No. 5,411,876.

[21] Appl. No.: 325,134

[22] Filed: Oct. 20, 1994

Related U.S. Application Data

[63] Continuation of Ser. No. 920,431, filed as PCT/US91/01039, Feb. 15, 1991, abandoned.

[51] Int. Cl.$^6$ ................................................ C12P 19/34
[52] U.S. Cl. ................................ 435/91.2; 435/6; 422/102
[58] Field of Search ................................ 435/91.2, 810, 435/6; 206/219, 568, 569; 935/16, 17, 18; 422/102

[56] References Cited

U.S. PATENT DOCUMENTS

| | | | |
|---|---|---|---|
| 4,251,506 | 2/1981 | Laby | 424/19 |
| 4,522,786 | 6/1985 | Ebersole | 422/56 |
| 4,683,195 | 7/1987 | Mullis et al. | 435/6 |
| 4,683,202 | 7/1987 | Mullis | 435/91 |
| 4,889,818 | 12/1989 | Gelfand et al. | 435/194 |
| 4,965,188 | 10/1990 | Mullis et al. | 435/6 |
| 5,314,809 | 5/1994 | Erlich et al. | 435/91.2 |

FOREIGN PATENT DOCUMENTS

| | | |
|---|---|---|
| 0258017 | 3/1988 | European Pat. Off. . |
| 0381501 | 8/1990 | European Pat. Off. . |
| 8806634 | 9/1988 | WIPO . |

OTHER PUBLICATIONS

Li et al., *PNAS* 87, 4580–4594 (1990).
Chou et al., *Nucleic Acids Res.* 20(7), 1717–1723 (1992).
D'Aquila et al., *Nucleic Acids Res.* 19(13),3749 (1991).
Handyside et al., *Nature* 344, 768–770 (1990).
Tomer et al., *Soil Sci. Soc. Am. J.* 53(1), 305–308 (1989).
Ward et al., 1989, Nature 341:544–546.
Newton et al., 1988, Nuc. Acids Res. 16(17):8233–8243.
Newton et al., 1989, Nuc. Acids Res. 17(7):2503–2516.
Shibata et al., 1988, J. Exp. Med. 167:225–230.
Kiyabu et al., 1989, Am J. Surg. Pathol. 13(3):221–224.

*Primary Examiner*—Stephanie W. Zitomer
*Assistant Examiner*—Kenneth R. Horlick
*Attorney, Agent, or Firm*—George W. Johnston; Patricia S. Rocha-Tramaloni; Stacey R. Sias

[57] ABSTRACT

Improvements to the polymerase chain reaction (PCR), a process for in vitro enzymatic amplification of specific nucleic acid sequences, can be achieved by changing the way that PCR reagents are mixed and the enzymatic reaction is started and by the replacement of mineral oil, commonly used as a vapor barrier to minimize solvent evaporation, by a grease or wax. The use of such mixtures allows for the delay of reagent mixing until the first heating step of a PCR amplification, thereby reducing the enzymatic generation of nonspecific products which occurs when a complete mixture of PCR reagents, with or without test sample, stands at room temperature or below. These mixtures increase the shelf-life of PCR reagents and increase protection of the laboratory environment against contamination by PCR product.

18 Claims, No Drawings

COMPOSITIONS AND METHODS FOR INHIBITING DIMERIZATION OF PRIMERS DURING STORAGE OF POLYMERASE CHAIN REACTION REAGENTS

This application is a continuation, of application Ser. No. 07/920,431, filed Oct. 8, 1992 abandoned, which is related to PCT/US91/01039 filed Feb. 15, 1991 which is now a continuation-in-part of U.S. patent application Ser. No. 07/481,501, filed on Feb. 16, 1990, abandoned.

FIELD OF THE INVENTION

The present invention describes novel compositions and methods for simplifying and improving the specificity of the polymerase chain reaction, a procedure for amplifying specific nucleic acid sequences which finds broad use in the fields of genetics, molecular biology, cellular biology, analytical biochemistry, clinical chemistry, and forensic science.

BACKGROUND OF THE INVENTION

The polymerase chain reaction (PCR) is a chemical method of increasing by many orders of magnitude the concentration of a specific nucleic acid sequence in a test sample. The PCR process is disclosed in U.S. Pat. Nos. 4,683,195; 4,683,202; and 4,965,188, incorporated herein by reference.

In PCR, a test sample believed to contain one or more targeted nucleic acid sequences is combined in a total volume of usually about 20–200 μl with the following reagents: an aqueous buffer, pH 8–9 at room temperature, usually also containing approximately 0.05M KCl; all four common nucleoside triphosphates (e.g., for DNA polymerase, the four common dNTPs: dATP, dTTP, dCTP, and dGTP) at concentrations of approximately $10^{-5}M$–$10^{-3}M$; a magnesium compound, usually $MgCl_2$, usually at a concentration of about 1 to 5 mM; a polynucleotide polymerase, preferably a thermostable DNA polymerase, most preferably the DNA polymerase I 4,889,818, incorporated herein by reference), usually at a concentration of $10^{-10}$ to $10^{-8}M$; and single-stranded oligonucleotide primers, usually 15 to 30 nucleotides long and usually composed of deoxyribonucleotides, containing base sequences which are Watson-Crick complementary to sequences on both strands of the target nucleic acid sequence(s). Each primer usually is present at a concentration of $10^{-7}$ to $10^{-5}M$; primers are synthesized by solid-phase methods well known in the an of nucleic acid chemistry.

In the simplest form, PCR requires two primers for each target sequence. These primers, when annealed to the opposing target strands, have their 3' ends directed toward one another's hybridization sites and separated by about 100 to 1,000 nucleotides (occasionally up to about 10,000 nucleotides). The polymerase catalyzes magnesium-dependent, template-directed extension of each primer from the 3' end of the primer, incorporating nucleoside monophosphates into the growing nucleic acid and releasing pyrophosphate.

This extension reaction continues until the polymerase reaches the 5' end of the template strand to which the extended primer was annealed, at which point the polymerase is free to bind to another primer-template duplex and catalyze extension of that primer molecule; the extension reaction also stops if the reaction mixture is heated to temperatures sufficient to separate the template from the extended primer before the enzyme has reached the 5' end of the template. After the enzyme has worked long enough to transform a large fraction of the primer-template duplexes into double-stranded nucleic acid, the latter can be denatured at high temperature, usually 90° to 100° C., to create two single-stranded polynucleotides, which, after cooling to a temperature where they can be annealed to new primer molecules, serve as templates for another round of enzyme-catalyzed primer extension. Because both DNA strands serve as template, each round of nucleic acid replication approximately doubles the concentration of the specific nucleic acid sequence defined at its ends by the two primer sequences. Therefore, the total concentration increase in the target nucleic acid sequence in a PCR amplification is by a factor of approximately $2^n$, where n is the number of completed thermal cycles between a high temperature where double-stranded DNA is denatured and a lower temperature or set of temperatures (40° to 75° C.) where primer-template annealing and primer extension occur.

Although one can move PCR reaction tubes manually back and forth between thermostated baths in the two temperature ranges, PCR most commonly is performed in an automated temperature-controlled machine, known as a "thermal cycler," in which a microprocessor is programmed to change the temperature of a heat-exchange block or bath containing reaction tubes back and forth among several specified temperatures for a specified number of cycles, holding at each temperature for a specified time, usually on the order of one-half to two minutes. Such a thermal cycler is commercially available from Perkin Elmer Cetus Instruments. The total cycle time is usually less than 10 minutes, and the total number of cycles is usually less than 40, so that a single, multi-cycle amplification, amplifying the targeted nucleic acid sequence $10^5$ to $10^{10}$ times, normally takes less than seven hours and often less than four hours.

The practical benefits of PCR nucleic acid amplification have been rapidly appreciated in the fields of genetics, molecular biology, cellular biology, clinical chemistry, forensic science, and analytical biochemistry, as described in the following review volumes and articles: Erlinch (ed.), 1989, *PCR Technology*, Stockton Press (New York); Erlich et al. (eds.), 1989, *Polymerase Chain Reaction*, Cold Spring Harbor Press (Cold Spring Harbor, New York); Innis et al., 1990, *PCR Protocols*, Academic Press (New York); and White et al., 1989, *Trends in Genetics* 5/6:185–189. PCR can replace a large fraction of molecular cloning and mutagenesis operations commonly performed in bacteria, having advantages of speed, simplicity, lower cost, and sometime increased safety. Furthermore, PCR permits the rapid and highly sensitive qualitative and even quantitative analysis of nucleic acid sequences, often with greatly increased safety because so much PCR product is made that nonisotopic detection modes suffice.

Despite rapid and broad adoption of PCR by a range of biological and chemical disciplines, PCR still possesses several practical limitations that must be overcome for full realization of the analytical and synthetic potentials of the process. Some of these limitations are discussed in turn, below.

Many amplifications yield nonspecific side products differing in size and sequence from the sequence targeted by the primers used. Sometimes nonspecificity is caused by mis-priming, where primers have been annealed to non-target sequences, also present in the nucleic acid of the test sample similar to the target sequence. Although the genomic DNA commonly contained in PCR test samples has customarily been thought to be completely double-stranded, procedures used to prepare DNA for amplification appear to render that DNA, to a large extent, single-stranded. Single-stranded DNA is especially susceptible to mis-priming if mixed with a complete set of PCR reagents at ambient or sub-ambient temperatures. Many PCR reactions also yield primer dimers or oligomers, double-stranded side products containing the sequences of several primer molecules joined end-to-end, the yield of which correlates negatively with the yield of amplified target sequence. "Low-copy-number" PCR, wherein the total number of initial target sequences is less than about 1,000, is especially prone to primer dimerization and mispriming, which reduce specific product yield, yield precision, and amplification specificity.

The high amplification factor and resulting high sensitivity of PCR renders the process especially vulnerable to back contamination, where amplified target from one reaction is accidentally transferred into a subsequent reaction using the same primers and gives a false-positive result in the later reaction.

In principle, PCR could be performed several times faster than current practice allows, being rate limited in part by the speed of temperature change during thermal cycling. Clinical diagnostic applications of PCR would especially benefit from total amplification times of 30 to 60 minutes instead of several hours.

Lower PCR costs and increased speed and precision could be obtained if the reagents could be mixed in large batches, aliquoted into the small reaction tubes (usually one-half ml total capacity containing 20 to 200 µl), and stored for long periods between preparation and use without loss of amplification efficiency.

The heretofore standard PCR art has called for covering the aqueous reaction mixture with 50 to 100 µl of mineral oil to prevent solvent evaporation during the several hours of heating. The mineral oil overlay introduces several practical problems: (a) mineral oil contamination of reaction mixture samples withdrawn for post-PCR analysis, often requiring extraction with hazardous water-immiscible organic solvents to avoid interference with post-PCR processing; (b) a retardation of thermal equilibration during thermal cycling (because of the significant heat capacity of the oil layer), increasing the total cycle time; and (c) occasional introduction from some batches of mineral oil of impurities which appear to inhibit PCR, necessitating rigorous quality control of mineral oil.

The present invention significantly mitigates the limitations of PCR discussed above, by several surprisingly simple modifications of PCR practice and materials. Because primer dimer and oligomer formation can occur whenever all of the PCR reagents are mixed, even at ambient and sub-ambient temperatures in the absence of thermal cycling and in the absence of target DNA, segregation of at least one reagent from the others in a way such that all reagents do not come together before the first amplification cycle can reduce primer oligomerization and, in doing so, can greatly extend the shelf-life of the incomplete reagent mixture without greatly complicating final reaction set-up. Such segregation also can minimize mis-priming during the poorly controlled interval over which PCR reagents and test sample customarily are mixed and stored at ambient or subambient temperatures before the start of thermal cycling, especially if segregated reagents and test sample are introduced into the PCR reaction tube with minimal mixing.

Several chemical properties of magnesium coffer special advantage to segregating the magnesium compound from the other PCR reagents (as opposed to segregating enzyme, primers, or dNTPs) when setting up a PCR amplification. Fatty acid salts of magnesium are potentially soluble in oil, grease, or wax, yet also potentially water extractable when the organic layer is contacted with the hot aqueous reagents during PCR. That way reagent segregation and reaction tube preparation can be simplified by incorporation of the magnesium into the organic layer rather than preparation of a separate aqueous reagent which must be added. Being inorganic, magnesium salts need not be prepared and stored with special precautions against microbial contamination, a common problem with mixtures containing nucleoside triphosphates, enzyme, or primers. The phosphatases and phosphodiesterases which degrade nucleoside triphosphates and primers often are magnesium-requiring, so that storage of the biological reagents without magnesium (possibly also with a trace of chelator to bind any small amount of magnesium present) improves shelf life and resistance to contamination by enzymes or by microbes which secrete the enzymes. Segregation of any potassium salt with the magnesium compound and away from the protein and nucleic acid also improves resistance to microbial consumption of reagents, because potassium ion also is needed for cell growth.

The present invention provides an especially effective mode of reagent segregation by providing means to replace the mineral oil overlay with a layer of grease or wax, the solidity of which at room temperature or below creates a barrier against mixing of aqueous reagents segregated above and below the grease or wax layer. Thermal cycling turns the solid barrier into a lighter-than-water liquid of low viscosity, which is displaced by an aqueous layer above; the upper aqueous layer contains all PCR reagents not present in the lower aqueous layer. Consequently, reagents previously segregated mix to create a complete reaction with the help of the considerable thermal convection which accompanies heating of the reaction tube. The melted grease or wax creates a vapor barrier to minimize solvent evaporation during thermal cycling and, upon cooling after amplification is complete, re-forms a solid barrier which, among other things, reduces the ease of PCR product dispersal into the environment when reaction tubes are opened, thereby reducing the likelihood of back-contaminating later reactions.

A photo-sterilization process to prevent back-contamination has been developed and involves the irradiation of psoralen and isopsoralen derivatives to photo-sterilize PCR product in a way which permits post-PCR analysis but prevents use of that product as a template in subsequent amplifications. However, the psoralen and isopsoralen photoreagents, commonly added before amplification, appear occasionally to inhibit PCR. Furthermore, the magnesium ion required for PCR is likely to reduce the affinity of photoreagent for double-stranded nucleic acid (Hyde and Hearst, 1978, *Biochemistry* 17:1251–1257), thereby reducing photoreagent efficiency or increasing greatly the photoreactant concentration required for practical photo-sterilization. The replacement of mineral oil with grease or wax, as provided by the present invention, permits a practical modification of the photo-sterilization procedure that prevents interference of the reagent with amplification of new target nucleic acid and should increase photoreaction efficiency. After amplification in the absence of photoreagent and after re-solidification of the grease or wax, the reaction tube can be opened without fear of contaminating the environment with PCR product. An aqueous solution of photoreagent and a chelating reagent which binds magnesium can be placed on top of the grease or wax. Closure of the tube and a simple brief heating step to melt the grease or wax allows mixing of photoreagent and chelator with PCR product; this mixture is now ready for optimal photo-sterilization, as the chelation of magnesium ion allows tight binding of photoreagent to nucleic acid.

After PCR amplification, common practice is to detect amplified nucleic acid by reacting the amplified nucleic acid with a reagent that carries an analytical signal generator or a reagent that facilitates separation of amplified nucleic acid from other components of the PCR reaction mixture. Such reagents are designed to bind very tightly to amplified nucleic acid, either because they include oligonucleotides with sequences complementary to pan of the target sequence (nucleic acid probes) or because they bind to molecules, such as fluorescein and biotin, which are conveniently attached to primers or the nucleoside triphosphates incorporated into PCR product. Signal-generating substances that might be included in such detection reagents comprise radioisotopes, fluorophores, chemiluminescent moieties, electrochemiluminescent catalysts, and catalysts in general, such as enzymes. Separation-promoting substances comprise antibodies, avidin, streptavidin, biotin, high-affinity haptens like fluorescein, magnetic particles, denser-than-water particles, latices capable of agglutination, and adsorbents capable of binding to either single-stranded or double-stranded DNA or to specific nucleic acid sequences.

Such detection reagents often are incompatible with PCR amplification, either because, like most proteins, they are inactivated by the prolonged heating in PCR or because, like most separation-promoting substances, they might inhibit PCR by removing reagents from solution. Therefore, it is generally beneficial to add PCR product detection reagents after amplification has been completed or almost completed. As in the case of photosterilization, the present invention allows such late addition to the PCR reaction tube to occur with minimal risk of contaminating the laboratory with amplified nucleic acid, because PCR product can be sealed beneath a layer of grease or wax.

Still another situation in which late addition to a PCR reaction is desirable concerns "nested primers," wherein PCR specificity is enhanced by following an initial amplification with an amplification using primers complementary to sequences not present in the original primers or primer-complementary regions but amplified by extension of the original primers. The present invention allows late addition of the internal primer pair of a nested primer system with much reduced concern about contaminating the laboratory environment with amplified nucleic acid. After such addition, only one or a few amplification cycles are needed to generate enough of the shorter PCR product to detect.

Many other situations exist in which late addition of a substance to a PCR amplification has beneficial effects on PCR sensitivity, specificity, convenience, and product analysis. In every case, the present invention advances the art by allowing that addition to occur: (a) under conditions where amplified nucleic acid is sequestered; and/or (b) at elevated temperature.

SUMMARY OF THE INVENTION

In a first aspect, the invention is a method of increasing the specificity of PCR amplification and of increasing the shelf life of pre-mixed PCR reagents, wherein PCR reagents (excluding the test sample containing the target DNA) are formulated as at least two non-overlapping subsets which can be stored for long periods of time (many months) without reaction or degradation, being brought together in a PCR reaction tube with minimal mixing shortly before (within a half hour of) thermal cycling. As described more fully below, this segregation can be achieved by (1) placing all but one (or more) essential PCR component in one container and the other essential component(s) in another container, (2) by placing all essential PCR reagents in a single container but having one or more essential reagents sequestered from the other essential reagents. This latter sequestration can be achieved by merely placing a barrier, such as a wax layer, between the reagent mixtures or by embedding one or more essential reagents in a matrix or gel, such as an agarose or acrylamide gel, or even a liposome.

In a preferred embodiment, all reagents except a magnesium compound are mixed in advance of amplification, and the complete reaction mixture is prepared in a way which minimizes mixing of the magnesium compound with the remaining reagents until the first amplification cycle is begun. Specifically, this embodiment comprises the layering of liquid solutions or suspensions of the magnesium compound, the magnesium-free reagents, and the test sample in the reaction tube, preferably in a way such that the test sample or a layer of solvent lies between the two reagent formulations. Preferably any potassium salt included in the PCR reaction mixture is formulated with the magnesium compound, not with the other reagents.

In a second aspect, the invention comprises compositions and methods which simplify the segregation of any subset of PCR reagents from the complementary subset, wherein each subset is formulated in an aqueous suspension or solution and a layer of grease or wax is placed between the two subsets before amplification. The grease or wax melts into a lighter-than-water liquid of low viscosity during the first amplification cycle, whereupon mutual displacement of the melted grease or wax and the aqueous layer above it and convective mixing of the now united aqueous reagents permits amplification.

In a third aspect, the invention comprises compositions and methods which simplify the segregation of any subset of PCR reagents from the complementary. subset, wherein one subset is incorporated into a lighter-than-water oil, grease, or wax which is layered on top of any aqueous suspension or solution of another subset. Heating during the first amplification cycle melts any grease or wax into a liquid, and heating of the aqueous layer results in extraction of the missing reagent subset from the lighter-than-water overlayer into the aqueous layer, convective mixing of the now united reagents permits amplification. One specific embodiment of this aspect of the invention consists of an emulsion of an aqueous solution or suspension of a subset of PCR reagents in the off, grease, or wax. Another embodiment is a solution of the subset of PCR reagents in the oil, grease, or wax. Specifically preferred PCR reagent formulations for dissolution in the oil, grease, or wax are magnesium fatty acid salts, and trialkylammonium salts of the nucleoside triphosphates and of the primers.

In a fourth aspect, the invention comprises compositions which improve the function of the second aspect of the invention by changing the physical properties of the grease or wax. Specific embodiments comprise: (1) a solution of surfactant in the grease or wax; (2) a solution of surfactant in the aqueous layer below the grease or wax; (3) an amplification container, the inner surface of which is hydrophilic; (4) a suspension of plastic particles in the grease or wax; and (5) a layer of plastic mesh suspended in the grease or wax. Preferred amplification containers with hydrophilic surfaces are plastic tubes which have been (a) coated with a surfactant, (b) plasma etched in an oxidizing environment, (c) treated with a strongly oxidizing liquid, or (d) cast from a resin melt to which surfactant has been added.

In a fifth aspect, the invention comprises any container for performing an aqueous chemical reaction which consists of a vessel and an amount of a wax sufficient to cover completely the exposed surface of the aqueous contents of the vessel, wherein the inner surface of the vessel is hydrophilic or the wax has been mixed with a nonionic surfactant.

In a sixth aspect, the invention comprises kits for PCR amplification of nucleic acids. These kits comprise the novel formulations of the PCR compositions of the present invention and can also comprise instructions for carrying out PCR with the compositions of the invention.

DETAILED DESCRIPTION OF THE INVENTION

The first four aspects of the invention improve the specificity of PCR amplification by preventing any catalytic reaction of nucleic acid polymerase with other reagents until the first amplification cycle. In particular, the formation of PCR side products known as primer oligomers, a reaction which occurs even at room temperature and below in the absence of nucleic acid template, is greatly reduced. Also disfavored is the mis-primed amplification of nonspecific targets when the test sample contains single-stranded DNA. Amplification of target PCR products often is increased and rendered more reproducible when side products are suppressed. The increased reaction specificity resulting from the invention often results in substantially pure amplified target sequence, greatly simplifying PCR product analysis and quantitation. For example, PCR product can be identified confidently on the basis of electrophoretic or chromatographic migration rate without resorting to slow, laborious, relatively unquantitative detection modes like nucleic acid probing. In particular, fast and highly automated HPLC analysis of PCR product now is practical.

The rust four aspects of the invention also simplify the bulk manufacture of ready-to-use PCR reagent formulations with shelf lives on the time scale of a week or more. Premixture of all reagents generally results in a shelf life of no more than a few days, apparently because of side reactions such as primer oligomer formulation, which occur at room temperature or below in the absence of template nucleic acid. As soon as at least one reagent is segregated from the others until the first amplification cycle, these side reactions cannot occur. Bulk manufacture of ready-to-use reagent formulations increases the speed, convenience, and reliability of PCR by relieving the user of the need to make careful mixtures of reagents at time of use. Often, time-of-use formulation entails mixing of small volumes and the preparation of just a few reaction mixtures at a time, reducing the inn-day and inter-day amplification precision.

The magnesium segregation (preferably also comprising potassium segregation) of the first aspect of the invention is an improvement over the segregation of other PCR reagents, such as enzyme, primers, or nucleoside triphosphates for several reasons. As the only non-biological, non-biodegradable, PCR reagent, the magnesium compound requires the least stringent (e.g., sterile) formulation and storage. Preferably, the other reagents are formulated together and stored in a manner which respects their biodegradability and greater chemical lability. Exclusion of an essential microbial nutrient, such as magnesium or potassium, from the biodegradable PCR reagents improves their resistance to biodegradation during storage. Storage of nucleoside triphosphates and single-stranded nucleic acid (e.g., primers) without magnesium is generally observed to improve shelf life, probably because many of the enzymes which might degrade them and which often are present as trace contaminants in reagents and on surfaces require magnesium for activity. The concentration dependence of magnesium activation of nucleic acid polymerases is such that low levels of magnesium leakage into a mixture of the other PCR reagents should result in negligible side reaction, whereas side reaction dependence on nucleoside triphosphate, primer, and enzyme concentrations is approximately proportional to reagent concentration.

The wax embodiment of the second aspect of the invention is a great improvement over the mineral oil currently used to minimize solvent evaporation during PCR, because wax, unlike oil, does not cling to the piper used to withdraw PCR product after amplification and, therefore, does not contaminate post-PCR detection reactions. According to the current art of PCR, mineral oil often is removed by time-consuming extraction with toxic or otherwise hazardous organic solvents. Replacement of mineral-oil with wax has another advantage quite apart from the function of wax as a vapor barrier and as a means of minimizing side reactions; the solid seal formed over the reaction mixture after amplification reduces the likelihood of contaminating the working environment with PCR product, thereby reducing the chance of back-contaminating subsequent reactions. Highly automated and precise large-scale manufacture of wax pellets which are rapidly and accurately dispensed to reaction tubes during manufacture or by the user also increases PCR convenience and reliability.

The second and third aspects of the invention are improvements over the simple layering embodiment of the fast aspect in that they eliminate the need for manual dexterity and close attention in setting up a complete reaction mixture. They also greatly extend the shelf life of complete reagent formulations, so that those formulations can be bulk manufactured and stored. If the heating of the fast amplification cycle is needed to combine all of the PCR reagents into an active mixture, one can manufacture a ready-to-use reaction tube which contains all reagents and requires only the addition of test sample and heating.

The compositions of the fourth aspect of the invention improve wax function in several ways. Surfactants in the wax or grease or underlying aqueous layer reduce the depth of the water-wax meniscus, thereby reducing the mass of wax or grease needed to cover completely the aqueous layer. A hydrophilic composition or coating for the inner surface of the reaction tube and the inclusion of surfactant in the wax or grease reduce the depth of the wax-air meniscus, thereby reducing the minimal required mass of wax or grease. A plastic mesh in the wax or grease reduces the depth of both menisci, and thereby the minimal required mass of wax or grease. This mesh also reduces the likelihood that a micropipet used to withdraw PCR product after amplification will be clogged with wax or grease and tends to prevent the spurting of PCR product when the wax or grease layer is penetrated. Plastic particles suspended in the wax or grease also reduce the overlayer mass, but their major benefit lies in imparting a slightly crumbly texture to the wax or grease, also reducing the clogging of pipet tips and the spurting of PCR product.

There are several advantages to minimizing the mass of an oil, grease, or wax layer over the aqueous layer in which PCR amplification occurs. The speed with which the contents of an amplification tube approach targeted temperatures in a thermal cycler varies inversely with the total mass of the tube and contents. Absent the present invention, the hydrophobic overlayer often has a mass approaching that of the aqueous layer. Maximum cycling speed is highly desirable in many PCR applications, especially for clinical diagnostics, and is promoted by minimizing the overlayer mass. Thicker layers of wax often resist penetration of pipet tips to withdraw PCR product, providing a tight seal around the tip which increases the likelihood that PCR product will spun from the amplification tube. Thicker layers increase the likelihood of plugging a pipet tip with grease or wax.

Ease of pipet penetration of a wax or grease layer, such that spurting of PCR product is avoided, is highly beneficial because such spurting can generate product-containing aerosols which can contaminate the laboratory environment, equipment, and reagents with PCR product. Because of the extreme sensitivity of PCR, even trace contamination can cause false-positive results in later amplifications.

Still another, major advantage of the invention is that the invention facilitates any manner of modification of PCR wherein reagents are added late in or at the end of the amplification to change the nature of the PCR process, facilitate the detection of amplified nucleic acid, or help to prevent back-contamination of subsequent amplifications. Such modifications include the following: PCR product cleavage, asymmetric PCR, nested priming, multiplex PCR, PCR product photosterilization, PCR product labeling, and the analysis of PCR product. Such reagents include the following: modified primers, internal primers, primers directed at new targets, metal ions, chelators, new enzymes, additional nucleic acid polymerase, modified or unusual nucleoside triphosphates, photoreagents, agents which bind specifically to amplified nucleic acid, nucleic acid probes, agents which capture, precipitate, or agglutinate amplified or single-stranded nucleic acid, and agents which help to generate analytical signals reporting on the presence of amplified nucleic acid. In every case, the present invention permits such late addition to occur with reduced concern that opening the PCR reaction tube might introduce amplified nucleic acid into the laboratory environment.

To promote understanding of the invention, definitions for the following terms are provided.

"Magnesium compound" refers to a substance containing magnesium in a form such that divalent magnesium ($Mg^{+2}$) is released into any aqueous solvent of pH (>-9 heated in contact with the substance to a temperature between about 50° C. and 100° C. for an interval of approximately 0.5 to 5 minutes.

"PCR reaction tube" refers to any container suitable for holding PCR reagents and test sample during a PCR amplification. In some contexts, the term also comprises the contents of the container. The deeming features of a container suitable for holding PCR reagents and test sample during a PCR amplification are that the container is made of a material which does not inhibit PCR, that can withstand temperatures in the range of about 20° C. to 100° C. while retaining substantially the same size and shape, and that can, together with any liquid contents, be capable of completing 40° C. temperature changes in the 50°–100° C. range in an interval of not more than about four minutes. Preferably, the container also will have a tightly fitting lid, which blocks water vapor or liquid escape from the container as well as container of the reaction with potentially nucleic acid-containing aerosols and dust from the laboratory environment. PCR reaction tubes commonly are molded from polypropylene, have sizes appropriate to contain 20–200 μl reaction mixtures, and have a tightly fining cap. PCR reaction tubes also commonly have shapes which fit tightly in the wells machined in the metal heating blocks used to control reaction temperature in most commercially available thermal cyclers. PCR reaction tubes most commonly have the size and shape of microcentrifuge tubes with 500–600 μl capacity; the bottom half is conical while the top half is cylindrical.

"Thermal cycler" refers to an automated device for controlling the PCR reaction temperature within the limits required for primer annealing, primer extension, and product denaturation; these limits normally are about 40° C. and about 100° C. The cycler changes the reaction temperature in a repeating manner, spending intervals of about 0.2 to 10 minutes at each temperature and requiring up to several minutes to move from one temperature to the next. Commonly thermal cycler temperature is under programmable microprocessor control, so that the user specifies in advance the number of cycles, the number of different incubation temperatures in each cycle, the value of each temperature, the incubation interval at each temperature, and often the transit time between temperatures. Thermal cyclers transfer heat into and out of PCR reaction tubes by contacting tubes with circulating thermostated air, circulating thermostated liquid, a thermostated metal block, or radiation from an infrared or microwave source.

"Plastic" refers to a polymer containing carbon and some combination of hydrogen, oxygen, nitrogen, fluorine, or much more rarely, other elements (such as sulfur), wherein the polymer is fabricated into a form (e.g., pellet, thread, sheet, rod, mesh, bead, or tube), which is water-insoluble and substantially water-impermeable. For the purpose of the present invention, useful plastics include polyethylene, polypropylene, polymethylpentene, polyester, nylon, fluorocarbons, fluorinated hydrocarbons, polymethylmethacrylate, and polystyrene.

"Plasma etching" and "corona discharge" are processes for modifying surfaces, especially plastic surfaces, by subjecting them, in a closed container often at subatmospheric pressure, to a highly corrosive atmosphere of electrons and atomic or molecular ions, produced by electrical excitation of the gas. Depending on the gases present in the atmosphere, different chemical modifications of the surface may result. For the purpose of the present invention, the atmosphere will include oxygen or water vapor, so that an exposed plastic surface becomes substantially oxidized and gains increased hydrophilicity.

"Liquid handling system" refers to an automated device for rapidly and precisely delivering liquid volumes in the approximate range of 1–100 μl, comprising some combination of liquid reservoirs, pumps, tubing, delivery tips or nozzles, heaters, movable heads or carriages for positioning the delivery tips in three dimensions, and control of time, volume, temperature, and position of delivery.

"Oil" refers to a water-immiscible organic substance, liquid at temperatures below about 40° C., which has a lower density than water. "Mineral oil", also known as liquid petrolatum and paraffin oil, is a colorless, optically clear, mixture of high molecular weight hydrocarbons with a density near 0.84 g/mL, widely available commercially and commonly used as a vapor barrier over PCR reactions.

"Grease" refers to an organic substance, solid or semi-solid but very soft at temperatures below about 40° C., which melts in the 40°–80° C. range to form a liquid which has a lower density than water. A typical grease is white petrolatum (e.g., Vaseline® Petroleum Jelly), a mixture of high-molecular-weight hydrocarbons.

"Wax" refers to an organic substance, solid but much harder than greases at temperatures below about 40° C., which melts at somewhat higher temperatures to form a liquid which has a lower density than water. Waxes tend to adhere to solid (e.g., plastic) surfaces more weakly than greases and oils do. Typical pure compounds which are useful waxes include eicosane ($C_{28}H_{42}$), octacosane ($C_{28}H_{58}$), cetyl palmitate ($C_{32}H_{64}O_2$), and pentaerythritol tetrabehenate ($C_{93}H_{180}O_8$). Typical useful wax mixtures include paraffin, Paraplast (tradename of Sherwood Medical), Ultraflex (tradename of Petrolite Corporation), and BeSquare 175 (tradename of Petrolite Corporation). Waxes can be prepared by mixing pure or mixed waxes with one another or with greases or oils in any ratios which preserve the relative hardness and reduced stickiness characteristic of a wax.

"PCR reagent" refers to any of the following materials which is necessary for PCR amplification: nucleoside triphosphate (at least four are needed; for example, dATP, dTTP, dCTP, and dGTP if a DNA polymerase is used), oligonucleotide primer (normally at least two are needed, defining by sequence complementarity to the two ends of the target sequence to be amplified), a magnesium compound (normally $MgCl_2$), and a DNA polymerase (normally *Thermus aquaticus* [Taq]polymerase I). PCR reagents may include nucleoside triphosphate analogues, such as dITP and 7-deaza-dGTP.

"Test sample" is any liquid preparation (solution or suspension) which might contain nucleic acid targeted by primers included among the PCR reagents, wherein that nucleic acid is in a chemical and physical state suitable for PCR amplification.

A "subset" of PCR reagents is any combination of the above reagents which lacks at least one essential reagent and therefore will not sustain PCR amplification.

"Complementary subsets" of PCR reagents are subsets which, when combined, complete the above list and therefore in combination sustain PCR amplification in the presence of the target nucleic acid sequence. Complementary reagent subsets are said to "complement" one another.

"Activity" in PCR refers to the ability of a subset of PCR reagents to sustain amplification of a specific target when combined in a PCR reaction tube with a buffer, the complementary reagent subsets, and a test sample containing that target and subjected to thermal cycling under conditions known to give amplification when all PCR reagents, buffer, and test sample are mixed immediately before cycling. "Full activity" implies that the quantity of specific PCR product approximates the maximum amount ever seen under the particular amplification conditions.

"Specificity" in PCR amplification refers to the generation of a single, "specific," PCR product with the size and sequence predicted from the sequences of the primers and the genomic or transcribed region of nucleic acid to which the primers were designed to anneal in a base-complementary manner. "Nonspecific" PCR product has a size or sequence different from such prediction. PCR "target" is that genomic or transcribed region of nucleic acid, the ends of which are base-complementary (with proper orientation) to a pair of primers included in a complete set of PCR reagents. "Proper orientation" is for the two primers to anneal to opposite strands of double-stranded target with their 3' ends pointing toward one another, normally with an intervening region in the approximate size range of 50–10,000 nucleotides. Such primers are said to "target" the genomic or transcribed sequence to the ends of which they are base-complementary.

"Layering" of PCR reagents or test sample or solvent refers to the process of delivering liquid formulations of different reagent subsets or test sample or solvent to a PCR reaction tube in a way which minimizes their mixing without interposition of an impermeable barrier (e.g., of wax or grease) between them.

"Vapor barrier" refers to a layer of oil, grease, or wax on top of the aqueous compartment of a PCR reaction which covers a large enough fraction of the exposed aqueous compartment surface to reduce substantially evaporation of water from that compartment during thermal cycling. Vapor barrier coverage is "complete" if, for an aqueous compartment of approximately 20–200 μl, 30 cycles of PCR amplification distill no more than about 2 mg of water to the walls and cap of a PCR reaction tube above the level of the vapor barrier.

"Liquid barrier" refers to a layer of grease or wax, which, at temperatures up to at least about 40° C. and not more than about 90° C., suffices to block mixing of aqueous compartments on either side of the layer for an interval of at least approximately 15 minutes. Liquid barrier coverage is "complete" if this 15 minute criterion is met.

"Thermal cycling" in PCR refers to the process of systematically and repetitively changing the temperature of a PCR reaction mixture in the approximate temperature range of 40°–100° C. to effect alternating denaturation of double-stranded DNA and primer annealing to single-stranded DNA followed by primer extension.

"Surfactant" is a substance which reduces the interfacial tension between water or aqueous solutions and hydrophobic solids or liquids like polyolefin plastics, oils, greases, and waxes. Surfactants are composed structurally of covalently joined hydrophilic and hydrophobic moieties. "Nonionic surfactants" contain no positively or negatively charged moieties. Typical nonionic surfactants include the following families of structural homologues: "Span" (trademark of Arias Chemical Industries: fatty acid mono-, di-, or triesters of sorbitan); "Tween" (trademark of Atlas Chemical Industries: polyoxyethylene ethers of fatty acid esters of sorbitan); "Brij" (trademark of Arias Chemical Industries: polyoxyethylene ethers of fatty alcohols); "Myrj" (trademark of Arias Chemical Industries: polyoxyethylene esters of fatty acids); and "Triton" (trademark of Rohm and Haas Company: alkylaryl polyoxyethyl ethers). Specific nonionic surfactants which are preferred for the present invention include Tween 85 (polyoxyethyl sorbitan triOleate) and Tween 65 (polyoxyethyl sorbitan tristearate). These two commercially available surfactants are just examples of a structural class known as "polyoxyethyl sorbitan triacylates," wherein polyoxyethyl chains of various lengths and three fatty acid residues of various sizes and structures are covalently attached to one sorbitan moiety.

For the purpose of the present invention, a "hydrophilic" surface is one which, when on the inner wall of a robe, shows a concave-upward meniscus when water partly fills the tube.

"Magnesium fatty acylate salt" refers to a compositions containing a 1:2 molar ratio of $Mg^{+2}$ to the conjugate base of a fatty acid. Representative fatty acids include butyric ($C_4H_8O_2$), caproic ($C_6H_{12}O_2$), caprylic ($C_8H_{16}O_2$), capric ($C_{10}H_{20}O_2$), and laurie ($C_{12}H_{24}O_2$) acids.

Choosing PCR primer sequences, preparing DNA-containing test samples, PCR reagents, and PCR reaction mixtures, designing and running PCR thermal cycles, and analyzing PCR product quantitatively or qualitatively are well known procedures in PCR art. A preferred mode for carrying out the first aspect of the invention is to combine in the PCR reaction tube a buffer, polymerase, dNTPs, and primers in an aqueous solution approximately twice as concentrated as is desired in the final reaction mixture and to layer on top of this "pre-mix," in any order, a stock solution of $MgCl_2$, a test sample believed to contain target DNA sequence, and sufficient mineral oil to form an effective vapor barrier, such that the combined volume of $MgCl_2$ and test sample approximates that of pre-mix, and the final $MgC_2$ concentration is approximately optimal for amplification of the specific target sequence defined by the primers. Although the pre-mix is substantially magnesium-free, the pre-mix may contain magnesium at a concentration less than about $10^4 M$ without sustaining PCR amplification in advance of adding the much larger amount of magnesium initially segregated from the pre-mix. A preferred order of layering is to interpose the test sample between the pre-mix and the $MgCl_2$, adding the mineral oil last, as this order maximizes the segregation of the complementary reagent subsets. Layering preferably is performed with all components at room temperature, delivering the components to the walls of the reaction tube slowly, so that minimal mixing of the different components occurs during addition. Preferably, reaction tubes are made up in this way within about 30 minutes of starting amplification (the shorter the time the better). Also preferably, the first step in thermal cycling will be the fastest possible heating of the PCR reaction tube from room temperature to 90°–100° C., to ensure rapid and complete convective mixing. The stability of reagent layers before heating can be increased by incorporating in the lowest layer a chemically inert, nonionic, den sifter such as sucrose at a concentration between about 1% and 20% by weight.

The replacement in the PCR reaction tube of mineral oil by grease or preferably wax leads to the second aspect of the invention, which is a preferred mode of effecting the first aspect of the invention. Once a layer of wax or grease seals the top of an aqueous solution of a subset of PCR reagents ("pre-mix"), an aqueous solution of the complementary reagent subset (preferably including a magnesium salt) can be added on top of the wax or grease without any concern that poor manual control will result in reagent mixing before thermal cycling begins. Test sample can be added before or after the wax or grease barrier is formed. Adding test sample afterward usually is more convenient, if only because large batches of reaction tubes containing wax- or grease-covered pre-mix can be made up efficiently in advance and stored for periods of days to months, preferably at 0°–5° C., so that test samples are added only as PCR reactions are needed. In this manufacturing mode, one preferably adds on top of the wax or grease barrier the reagent(s) missing from the aqueous layer beneath the barrier after the barrier has been fortrod and before storage, so that the user needs only to add test sample immediately before thermal cycling. If the manufactured tubes contain everything except test sample, the wax or grease barrier must be durable enough to prevent reagent transfer across the barrier on the storage time scale, as some wax or grease layers may be strong enough to leak negligibly on the time scale of an hour or less but show significant leakage on the time scale of a day or more. One way to test leakage across the barrier is to include in the upper aqueous layer a water soluble, wax-insoluble dye such as bromphenol blue at a concentration of 0.01% to 0.1%, checking visually for signs of dye movement into the lower aqueous layer.

A preferred mode of creating the wax or grease barrier is to add to the reaction tube a solution of the reagent subset which is to lie beneath the barrier and a mass of wax or grease sufficient to form a vapor barrier and then to incubate the tube, preferably closed, for sufficient time at a sufficient temperature for the wax or grease to melt and form a homogeneous liquid layer above the aqueous reagent solution. The tube is then returned to room temperature for at least enough time for the wax or grease to solidify. The incubation temperature must be above the wax or grease melting point but preferably will not be more than 10° C. above the melting point and in no case above about 90° C., so that the possibility of thermal inactivation of polynucleotide polymerase, if present in the pre-mix solution, is minimized. Normally a melting time between about 30 seconds and about five minutes should suffice, and a cooling time of at least about five minutes is preferred for the barrier to harden completely. Rapid cooling, for example in an ice bath, appears to be undesirable because the wax or grease is less likely to cover the underlying aqueous compartment.

The mass of wax or grease preferably is minimized, using just enough to ensure complete coverage of the aqueous contents of the reaction tube after melting of wax or grease during thermal cycling has resulted in mixing of the aqueous layers above and below the barrier layer. Such coverage can be assessed by measuring how much water is distilled onto the walls and into the cap of the reaction tube during a PCR amplification. For example, after amplification, the tube can be weighed (preferably on an analytical balance accurate to 0.1 mg or less), the water deposited above the vapor barrier can be removed by gentle swabbing with a cotton-tipped stick, and the tube is then reweighed to determine the water removed. For standard PCR reaction volumes (20–200 µl), complete coverage results in distillation of less than about 2 mg of water to the tube surfaces above the vapor barrier. In general, the minimal mass of wax or grease required for complete coverage (maximal vapor barrier effectiveness) will vary directly with the total aqueous volume because the conical cross-section of typical PCR reaction tubes causes the surface area at the air-water interface to increase as the aqueous volume increases. Them are at least two reasons to minimize the mass of wax or grease: (1) the time required for thermal equilibration during cycling varies directly with total mass of the reaction tube and its contents, and (2) wax or grease in excess of the minimum mass needed to serve as an effective vapor barrier complicates the recovery of PCR product after thermal cycling, tending to clog the tip of the micropipet used to withdraw PCR product from the tube or (in the case of wax) creating a mechanically tough barrier requiring considerable pressure to effect micropiper tip penetration. Normally the wax or grease barrier is penetrated for sample withdrawal simply by applying light manual pressure to the top of the barrier (usually at the center, where it is thinnest) by an ordinary air-displacement or positive-displacement micropipet or "sampler." However, a wax barrier also can be breached by freezing and thawing a wax-covered aqueous layer. The expansion of the ice fractures the wax so that pipets easily penetrate it; a short centrifuge spin in an angle rotor helps to assure wax fragmentation.

Wax is preferred over grease because wax is much less likely to clog or coat micropipet tips. Being tougher than grease, wax can effectively segregate PCR reagent subsets in a thinner layer, and, therefore, with less mass. Many wax compositions are effective for the purpose of the present invention, including the following: paraffin (55°–61° C. melting range), eicosane, Paraplast, Ultraflex, octacosane, cetyl palmitate, pentaerythritol tetrabehenate, and "BeSquare 175" Wax. Mixtures of these waxes in various proportions, mixtures of these waxes with grease such as white petrolatum, and mixtures of these waxes with mineral oil also may be advantageous. Although individual wax preparations may prove unsuitable, either because they contain substances inhibitory to PCR or because, coming from biological sources, they may contain contaminating DNA capable of giving false positive PCR responses, in general almost any wax melting between about 40° C. and about 80° C. might serve as both a barrier layer for segregating PCR reactants before thermal cycling and as a vapor barrier for minimizing water evaporation during thermal cycling. Waxes, greases, or oils prepared from petroleum are preferred over materials derived directly from animals or plants to minimize the chance of contamination with nucleic acid, phosphatases, nucleases, or proteases. They must have densities less than that of the aqueous solutions used in PCR if they are to serve as a vapor barrier during amplification. Heavier-than-water waxes and greases (e.g., containing silicon, phosphorus, sulfur, or halogen atoms) also would serve the function of separating PCR reagent subsets until the first amplification cycle. Although unlikely to work as a vapor barrier after heating, they might beneficially sink to the bottom of a reaction tube when a vapor barrier is not needed, and in doing so might promote mixing of previously separated aqueous reagents. However, layering a heavier-than-water molten grease or wax over an aqueous compartment requires considerable expertise.

The simplest way to test the suitability of a wax for the present invention is to (1) combine in a 500 µl polypropylene microcentfifuge tube approximately 15 mg of the wax and approximately 50 µl of an aqueous solution containing all PCR reagents except a magnesium compound; (2) cap the tube and immerse the tube in a water bath at a temperature exceeding the wax melting point for a sufficient interval (approximately one minute) for the wax to melt completely; (3) remove the tube from the water bath to cool to room temperature; (4) add on top of the wax approximately 50 µl of a mixture of $MgCl_2$ and a test sample containing DNA targeted by the primers included in the PCR reagents; (5) perfoE a PCR amplification using thermal cycle conditions appropriate for the particular combination of primers and target DNA; and (6) analyze the post-PCR reaction mixture for the presence of PCR product of the predicted length containing a predicted intervening (non-primer) sequence by methods well known in the field of molecular biology. The concentrations of all PCR reagents and of target DNA should be within ranges already understood to give effective amplification when mineral oil, usually in the mass range to 40 to 80 mg, is used instead of wax.

During this testing procedure, several adjunct analytical procedures help to optimize the results. Visual examination of the wax layer before adding $MgCl_2$ and DNA and after thermal cycling helps to verify that the mass of wax is large enough to serve the liquid- and vapor-barrier functions. If the mass of wax used is insufficient to cover the aqueous layer completely, the mass should be increased until coverage of the aqueous layer is complete. Gravimetric measurement of the water distilled past the wax into the upper regions of the reaction tube (by weighing the tube before and after using an absorbent swab to remove the water) also helps to evaluate vapor barrier effectiveness. Distillation of more than about 2 mg of water indicates that increasing the mass of wax may help. Probing the hardness and toughness of wax layer with a micropiper tip may also indicate whether the wax preparation is useful for PCR; preferably the sampler tip will penetrate the wax without clogging or causing wax to stick to its sides, and penetration will require little force and be easy to control. Certain anionic dyes, such as bromphenol blue in the concentration range of about 0.01% to 1% can be included in the aqueous layer above the wax or grease without interfering with PCR. Visual inspection of how well the dye has mixed in the aqueous layer below the wax or grease after the first cycle is effective for testing that the wax or grease does not impede mixing.

These tests enable one skilled in the arts of PCR and molecular biology to choose waxes, wax mixtures, and mixtures of waxes with oils and greases which serve optimally for segregating PCR reagents and for blocking solvent evaporation, and to find the optimal mass of wax for a particular combination of aqueous volumes above and below the wax barrier. If, in addition, a wax formulation and mass are needed to confer long-term storage stability to a wax-covered PCR reagent subset, with or without the long-term presence of the complementary subset above the wax layer, one need only perform these tests after different storage intervals between preparation and thermal cycling, preferably adding any missing reaction components (including target DNA) on top of the wax layer just before thermal cycling.

Especially preferred for the second aspect of the present invention is a solution in the wax of a surfactant, preferably nonionic, in the concentration range of approximately 0.1% to 1% by weight, prepared by melting the wax, adding the surfactant, stirring the mixture for a period of at least about one minute and then allowing the matter mixture to stand undisturbed for at least about 10 minutes before observing whether any surfactant has formed a separate liquid phase, usually denser than the wax. Phase separation shows that the nominal surfactant concentration exceeded the solubility of surfactant in the wax, suggesting that a lower nominal concentration should be used. Addition of surfactant generally lowers the mass of wax needed to form a complete liquid barrier and a complete vapor barrier, shown by titrating the minimum mass of wax needed to obtain complete coverage of an underlying aqueous layer, as described above. Preferred surfactants are ones which are not very water soluble, containing relatively small hydrophilic moieties and relatively large hydrophobic groups. Specifically preferred commercially available surfactants are Tween 85 and Tween 65. Novel polyoxyethyl sorbitan triacylate surfactants with polyoxyethyl chain length or fatty acid structure optimized for PCR vapor barrier performance may improve performance in various ways. For example, PCR thermal cycling of aqueous solvent beneath a surfactant-containing wax layer may result in some extraction of surfactant, possibly accompanied by wax, into the aqueous layer. This event can be analyzed by measuring the ultraviolet and visible absorbance spectra of the aqueous layer, as extracted surfactant forms miceliar particles with a characteristic light-scattering spectrum. Although extracted surfactant does not generally interfere with PCR or post-PCR analysis, it may be detrimental in specific instances. Shortening the length of the polyoxyethyl chain or increasing the length of the fatty acid from what is used in Tween 65 or Tween 85 should reduce surfactant water solubility and extractability during thermal cycling. Use of the second aspect of the invention may be improved also by incorporation into the wax or grease of an oil soluble dye such as Oil Red 0, Oil Blue N, Solvent Green, Fat Red, and Sudan Orange in the concentration range of about $10^{-3}$% to $10^{-1}$%. Such dyes do not interfere with PCR.

Inclusion in the bottom aqueous layer of 0.1–10% of a surfactant, also preferably -nonionic, may serve to improve the second aspect of the invention, again by reducing the mass of wax needed for complete coverage of the aqueous layer. Preferred surfactants are relatively water soluble ones, such as Tween 20 and Triton X-100, many of which do not appear to interfere with PCR.

Also especially preferred for the second aspect of the invention is the use of plastic PCR reaction tubes which have been manufactured or treated in such a way as to have a hydrophilic internal surface. This embodiment serves to reduce the mass of wax or grease needed for liquid barrier and vapor barrier function. Specific processes for making such tubes include (a) plasma etching or corona discharge in a chamber where the open tubes are exposed to an oxidizing atmosphere, (b) incubation of the plastic in a liquid oxidizing formulation such as Fenton's reagent, (c) inclusion of a surfactant in the molten resin from which the tubes are cast, and (d) coating the tubes with a surfactant. Surfactant coating of normally hydrophobic reaction tubes may be accomplished by the following steps: (1) dissolution of 0.1–10% (by weight) of the surfactant in a nonaqueous solvent such as 1-propanol, 2-propanol, or 1-butanol, (2) filling of the open tubes with the surfactant solution at 20°–30° C., (3) incubation of the filled tubes at 20°–30° C. for an interval of between about 1 and 30 minutes, (4) drainage of the incubated tubes to remove all bulk surfactant solution, and (5) air drying of the drained tubes at atmospheric or reduced pressure, at approximately 20°–60° C.

Not all surfactants are soluble in useful nonaqueous solvents to concentrations as high as 10%; some care should be used to assure that coating surfactant is completely dissolved. This coating procedure may be repeated at least about 10 times with the same surfactant solution, as it appears not to consume a significant faction of surfactant of each coating. Preferred nonaqueous solvents have boiling points between about 60° C. and 110°C. and dissolve surfactant to a concentration of at least about 1%. Preferred surfactants are Tween 65 and Tween 85. Corona discharge and plasma etch methods for treating plastics are reviewed in the following articles and books: Hoffman, 1988, *Journal of Applied Polymer Science: Applied Polymer Symposium* 42:251–265; Gombotz and Hoffman, 1987, *C.R.C. Critical Reviews in Biocompatibility* 4:1–42; Boenig, 1982, *Plasma Science and Technology*, Cornell University Press, Ithaca; Oskam, 1984, *Plasma Processing of Materials*, Noyes Publications, Park Ridge, N.J. Fenton's reagent is described in the following articles: Walling, 1975, *Accounts of Chemical Research* 8:125–131; Graf et al., 1984, *Journal of Biological Chemistry* 259:3620–3624; and Imlay and Linn, 1988, *Science* 240:1302–1309. When the second aspect of the invention is performed with hydrophilic reaction tubes, a preferred mode of supplying such tubes ready for use is to deliver to each tube a pellet of wax sufficient in mass to cover completely a specified aqueous reaction volume. Then the user needs only add an aqueous solution of a subset of PCR reagents, heat the tube several minutes at a temperature 5°–10° C. above the wax melting point, allow the tube to cool to room temperature or below, add on top of the newly formed wax layer a mixture containing the complementary PCR reagent subset and test sample, and start PCR amplification, respecting the need to keep the total aqueous volume below the rating for the mass of wax supplied.

The second aspect of the invention is most effective if, during the first cycle of thermal cycling, the reaction tube is heated as rapidly as possible from an initial temperature of about 0°–25° C. to a DNA denaturation temperature above 95° C. and below 100° C., preferably about 98° C., and is held at that high temperature for an interval between about 1 and 2 minutes. This process serves not only to melt the wax or grease and to denature the DNA in the test sample, but also to promote vigorous thermal convection currents in the newly combined upper and lower aqueous solutions so that all PCR reagents and the test sample DNA are completely mixed; incomplete mixture can reduce amplification efficiency. Other embodiments which help to ensure complete mixture are to include inorganic salts such as $KC_1$ in the upper PCR reagent subset and to exclude them from the lower, complementary subset, and to include a 1–20% concentration of a low molecular weight densflying agent such as sucrose in the upper aqueous layer. In general, it is useful to render the upper aqueous layer denser than the lower one, preferably excluding from both layers organic polymers or inert proteins such as gelatin, which tend to increase viscosity and thereby reduce convective turbulence. Still another way to promote convective mixing of top and bottom aqueous layers after the wax or grease has melted is to tilt the reaction tube at an angle of between about 10 and 30 degrees from the vertical after the wax or grease has been melted, allowing the barrier layer to solidify at this angle. After cooling, the top of the wax should be examined visually to assure that the bottom aqueous layer is completely covered, as tilting tends to thin the barrier layer.

The wax or grease layer of the second aspect of the invention can be thinned further by incorporation into it of polymeric particles or of relatively fine plastic mesh, two additives which also can reduce clogging of sampler tips. The mesh must be cut, conveniently with a punch, into disks with a diameter approximately equal to the inner diameter of the reaction tube at the top of the lower aqueous layer. As the bottom half of the customary tube is conical, this diameter, on the order of several millimeters, will depend on the volume of the lower aqueous layer. The composition and pore size of the mesh tolerate wide variance. Acceptable plastics include polyethylene, polypropylene, polymethylpentene, polyester, nylon, and various fluorocarbons; the pore size may vary from about 0.001 to about 1 mm. Nylon is somewhat less preferred, because nylon can bind nucleic acids, and fluorocarbons are somewhat less preferred because of greater density and cost. Polypropylene is most preferred, because it has the lowest density (most compatible with wax, grease, or oil), is highly hydrophobic, has a thermal tolerance matching that of the most commonly used PCR reaction tube material (also polypropylene), and is likely to be the cheapest. Polymethypentene is also especially preferred because of low density, high hydrophobicity, and high thermal tolerance, but pre-manufactured mesh may not be readily available commercially.

A wide variety of mesh compositions and opening sizes is available from Spectrum Medical Industries, Los Angeles. The shape, composition, diameter, and porosity of the polymeric particles also admit wide variance. Shapes may be irregular or spherical (the latter usually described as beads). Compositions can include any of the polymers listed above for meshes plus two polymers commonly used to make beads: polymethylmethacrylate and polystyrene. Diameter can range from about $10^{-3}$ mm to about 1 mm. Larger diameters (above 0.1 mm) are preferred because they are less likely to enter micropipet tips. Nonporous particles are preferred because they offer a much lower surface area to entrap PCR reagents which come in contact with the wax or grease layer. Preferably the particles have a density less than or very close to water, so that they are unlikely to drop from the wax or grease layer through the aqueous layer when the former melts into an oil. Examples of commercially available polymeric particles suitable for the present invention include polypropylene granule, 0.5 mm maximum size, from Goodfellow (Malvern, Pa.); chromatographic grade polypropylene and polyethylene spherical particles of diameter between about 0.01 mm and 0.15 mm from Polysciences, Inc. (Warrington, Pa.); Bio-Beads SM polystyrene-divinylbenzene and acrylic ester adsorbents, 20–50 mesh, from Bio-Rad (Richmond, Calif.); Ambeflite XAD polystyrene and acrylic ester adsorbents, 20–60 mesh, from Rohm and Haas (Philadelphia, Pa.); plastic or glass-coated plastic BioSpheres, 0.1 to 0.2 mm diameter, from Whatman BioSystems, Inc. (Clifton, N.J.); Rapid Cell P plastic or glass-coated plastic beads, 0.15–0.21 mm diameter, from ICN Biomedicals, Inc. (Cleveland, Ohio); and Polybead polystyrene microspheres and polymethylmethacrylate beads from Polysciences, Inc.

Some of these polymeric particles, especially those made of polystyrene or polymethylmethacrylate, will swell when contacted with low-molecular-weight solvents such as water and alcohols. Preferably, they are swollen at room temperature in a relatively water-insoluble organic solvent such as a liquid aliphatic hydrocarbon (pure or a mixture, such as petroleum ether or ligroin) so that they will not tend to absorb water at the interfaces between the aqueous layers and the grease or wax. Some of them may be supplied as aqueous slurries, already swollen in water, in which case preferably they are dehydrated by stirring at room temperature in successively less polar solvents like ethanol, acetone, and a liquid aliphatic hydrocarbon.

The concentration (in mass percent) of polymeric particles in the grease or wax permits considerable variability and can be optimized for any of several functional properties of the particle-wax/grease mixture. For example, various mass ratios of particle to wax or grease can be tested to find the one which provides complete vapor barrier protection to a fixed volume of the underlying aqueous layer with the least mass of overlayer. On the other hand, various mass ratios can be tested to find the range which imparts maximum or minimum resistance to penetration by a micropiper tip or maximum stability during long-term storage (for example, maximum resistance to magnesium penetration from an upper aqueous layer into a lower aqueous layer separated by a solidified mixture of polymeric particles and wax or grease).

Wax or grease barriers containing polymeric particles and especially disks of plastic mesh may benefit from solidification with the PCR reaction tubes tilted 10–30 degrees from the vertical, to promote mutual displacement of the barrier and an aqueous layer above it when the wax or grease in the former melts.

There are two major embodiments of the third aspect of the invention: (a) aqueous emulsion of a subset of PCR reagents in a wax or grease barrier covering an aqueous solution of a different reagent subset and (b) solution in the barrier of a PCR reagent subset. The melting of the barrier which accompanies thermal cycling breaks the emulsion, releasing the aqueous phase containing PCR reagents into the underlying aqueous layer, where thermal convection mixes all PCR reagents together with the test sample, preferably added as an aqueous solution above the barrier layer before cycling is started. Alternatively, dissolved PCR reagents in the barrier layer are extracted and mixed into the underlying aqueous layer, as the barrier layer melts and becomes less viscous and as thermal convection currents are established in both the underlying aqueous layer and the barrier layer. For these embodiments, it is especially preferred to minimize the mass of the barrier layer by any of the modes described above, singly or in combination: polymeric particles or mesh or surfactant in the barrier, hych-ophilic inner surface of the reaction tube, or surfactant in the aqueous layer. Minimizing the barrier mass, and, therefore, thickness, accelerates the equilibration of the aqueous and barrier layers and favors partitioning of any barrier-dissolved PCR reagents into the aqueous layer.

Water-in-grease or water-in-wax emulsions are made by methods well known in the field of material science, basically by high-speed mixing of appropriate volumes of an aqueous phase (in this case containing a subset of PCR reagents) and a melted grease or wax at a temperature above the grease or wax melting point, followed by rapid cooling of the homogeneous emulsion before it has a chance to phase-separate. Incorporation of a surfactant into either phase or both helps to stabilize the emulsion. Any of a large array of surfactants, preferably nonionic, are effective to this end, provided that they do not inhibit PCR and are used to concentrations stabilizing water- in-oil rather than oil-in-water emulsions. The an of forming emulsions is reviewed in the following volumes: Becker, 1966, *Emulsions: Theory and Practice*, 2nd Edition, Reinhold, New York; Sherman, 1968, *Emulsion Science*, Academic Press, New York; and Lissant, 1974 (Pans I and II) and 1984 (Pan III), *Emulsions and Emulsion Technology*, Marcel Dekker, New York.

Although practically any combination of PCR reagents is suitable for incorporation into a water-wax or water-grease emulsion, one reagent, a magnesium compound, is most preferred for dissolution in the wax or grease in the absence of emulsification. That is because salts of magnesium ion and the conjugate bases of relatively short-chain fatty acids, such as butyrate, caproate, caprylate, caprate, and laurate, have the dual properties of being acceptably soluble in oils to the level of 1–50 mM and of being much more soluble in hot water than in cold. In this manner, the magnesium fatty acid salt can be dissolved in a molten wax or grease, layered on top of an aqueous phase and fairly rapidly cooled (in an interval of about one minute) so that it is trapped in the hardened wax or grease before it is extracted into the warm water, and yet will be efficiently extracted when the multilayered mixture is heated to 95°–98° C. for a period of one to two minutes at the start of thermal cycling. To minimize extraction into the aqueous layer during casting of the barrier, it is preferred to use a wax or grease with the lowest practical melting point, preferably in the range of about 40°–50° C. Examples of such waxes include eicosane (m.p. 36°–38° C.), low-melting paraffin (m.p. 56°–61° C.), and mixtures of these two waxes or of eicosane with other, higher-melting, waxes. Oligonucleotide primers and dNTP's also can be rendered wax-soluble if transformed into their trialkylammonium (e.g., triethylammonium) salts. This reaction can be performed by passing the nucleotide, commonly available as its sodium salt, down a chromatographic column containing a cation exchange resin, such as Dowex 50, which has been equilibrated with a trialkylamine.

As the magnesium-fatty acylate salts in the $C_4$–$C_{12}$ size range are not generally available commercially, they must be synthesized, preferably by heating the fatty acid to a temperature in the approximate range of 60°–80° C. and adding one mole of magnesium oxide for every two moles of fatty acid, stirring for a sufficient period to assure complete dissolution (reaction) of the magnesium oxide. After cooling to room temperature, the magnesium fatty acylate salt can be stored over a desiccant such as $MgSO_4$ or $P_2O_5$ to remove all of the water produced in the reaction which is not evaporated during heating.

In one mode of realizing the third aspect of the invention, the PCR reagent subsets in the grease or wax and in the underlying aqueous phase are complementary, so that an additional aqueous PCR reagent formulation need not be prepared for placement above the grease or wax. In another mode, three PCR reagent subsets are required for complementation: one in the grease or wax and two aqueous formulations, one above and one below the grease or wax.

The latter mode is especially effective in preventing all PCR reagents from coming together in a single aqueous phase prior to the first cycle of a PCR amplification.

There are many ways to aliquot the wax or grease of the present invention into the PCR reaction tubes, whether or not the wax or grease contains surfactant, polymeric particles, a magnesium fatty acylate salt, or an emulsified aqueous solution of a subset of PCR reagents. The solid wax or grease can be weighed into separate tubes; the small masses involved, generally below 30 mg, require use of a balance with a precision of 1 mg or better, preferably 0.1 mg. However, a much faster and sufficiently precise method is to melt the wax or grease and deliver it volumetrically with a positive-displacement micropipet adjusted to deliver the minimum mass giving an effective vapor barrier. Preferably, the micropipet will have a glass tip, as plastic tips tend to capture wax or grease in a way which reduces precision. An example of a suitable variable-volume glass-tipped positive-displacement micropipet is the Micro/Pettor® manufactured by SMI. If the wax or grease is delivered to a solid surface at room temperature or below, it will solidify as a roughly hemispherical bead which is easily separated from the surface and delivered to a PCR reaction tube (e.g., with forceps). The colder the surface, the easier it is to separate the wax or grease bead from it. A convenient receptacle is a disposable weighing boat, available from many scientific supply companies. Once the wax or grease pellet and the appropriate volume of an aqueous solution of a subset of PCR reagents has been delivered to a PCR tube, the tube should be capped, heated to a temperature sufficient to melt the wax or grease for a period of about one minute, and cooled at room temperature to seal the wax or grease barrier over the aqueous layer.

Plastic micropipet tips can be rendered more suitable for aliquoting wax if they have been rendered hydrophilic as described above for PCR reaction tubes, e.g., by corona discharge or surfactant coating. Then plastic-tipped air-displacement samplers are adequately precise for wax delivery. The precision of wax delivery by plastic tipped air-displacement samplers also is improved by heating the wax at least 30° C. above its melting range. Preferred for the automated aliquoting of wax is a microprocessor-controlled multi-tipped air-displacement sampler like the ProPette® laboratory robot, supplied by Perkin Elmer Cetus Instruments. Automated or semiautomated rapid and precise manufacture of many thousands of wax beads at a time can be effected by delivering molten wax at a temperature approximately 5°–15° C. above its melting point by a pneumatically driven heated liquid dispenser (for example, under regulation by an Accura 1 regulator for Iwashita Engineering Incorporated), collecting wax beads on a rotating chilled drum from which they are scraped into a tray after hardening. For example, the drum can simply be a 2–3 liter glass bottle, 100–300 mm in diameter, filled with ice, rotating at about 1–3 rpm on a culture bottle roller (Wheaton Instruments Inc.).

Although the previous description has emphasized the creation of wax or grease barriers to enable the segregation of complementary PCR reagent subsets prior to thermal cycling, it must be realized that wax is such an improvement over the mineral oil vapor barrier commonly used in PCR that the modes of preparing and optimizing a wax barrier described above may serve well in PCR reactions where there is no desire to segregate reactants before thermal cycling. Then the wax, all PCR reagents, and the test sample may simply be mixed together in a reaction tube, preferably within several minutes of starting thermal cycling. As soon as the wax melts during the first cycle, the wax will form a vapor barrier to block solvent evaporation. When the reaction mixture cools at the end of thermal cycling, it will form a solid barrier to reduce the chance of unwanted PCR product dispersal, a barrier which can easily be penetrated by a micropiper for PCR product withdrawal. Furthermore, the art of forming and using wax or grease vapor barriers in containers with hydrophilic inner surfaces, or with inclusion of nonionic surfactant in the wax or grease, is disclosed herein in a manner enabling adaptation to non-PCR contexts, which benefit from any of the advantages listed herein. The major adjustment is of the mass of wax or grease to cover completely the exposed surface of the aqueous compartment in the preferred container.

Many of the advantages of the present invention can be achieved simply by packaging subsets of PCR reagents in different containers. In a preferred embodiment, this aspect of the invention is a kit that comprises (a) one tube that contains a pair of primers, a nucleic acid polymerase (preferably Taq polymerase), and one or more deoxyribonucleoside triphosphates (preferably dATP, dGTP, dCTP, and dTTP) in a suitable buffer; and (b) a tube that contains $MgCl_2$ (preferably in solution). The kit can also comprise instructions for carrying out the PCR process with the kit components. In particular, the instructions will describe how to mix the contents of tubes (a) and (b) with a test sample. In the most preferred embodiment, such a kit comprises (a) one tube that contains 50 µl of solution composed of 1.15 micromoles of Tris-HCl, pH 8.3; 5 micromoles of KCl; 17.25 picomoles of each primer, 21.6 nanomoles of each of the four deoxyribonucleoside triphosphates; and 2.875 units of Taq polymerase (PECI); and (b) one tube of 8.05 mM $MgCl_2$. Typical instructions for this kit would tell the user first to layer 50 µl of the $MgCl_2$ solution onto the top of the solution in tube (a), then to add two drops of mineral oil, then to add the sample DNA in a volume of 2 to 40 µl on top of the $MgCl_2$ layer, and to place the sample in a PECI Thermal Cycler as soon as possible (under 30 minutes).

In yet another embodiment of the invention, a gel or other matrix containing one essential PCR reagent, i.e., Taq polymerase, is layered onto the other components of the PCR mixture (except sample), and the gel or matrix is composed such that, upon sample addition and heating, the gel or matrix melts and so reconstitutes a complete PCR mixture. In one embodiment, the gel is agarose containing Taq polymerase.

Although this disclosure has focused on improvement of PCR performance, the invention is applicable to other modes of enzymatic replication of nucleic acids, such as the transcription-based amplification system (Kwoh et al., 1989, *Proc. Natl. Acad. Sci. USA* 87:1874), amplification systems based on nucleic acid ligase (Wu and Wallace, 1989, *Genomics* 4:560, and Barringer et al., 1990, *Gene* 89:117), and amplification systems based on ribonuclease H cleavage of a DNA-RNA-DNA probe annealed to a nucleic acid target. Characteristic features of an in vitro nucleic acid amplification or detection system which would experience improved specificity through application of the invention are the following:

(a) a nucleic acid primer or probe, usually an oligonucleotide, must be annealed to a target nucleic acid sequence;

(b) the maximum, or "stringent", temperature for such annealing must lie above ambient temperature (approximately 20°–30° C.);

(c) a catalyst, usually an enzyme, must act on the annealed nucleic acid complex;

(d) the catalyst must be active at the stringent annealing temperature; and (e) the catalyst must retain significant activity at ambient temperature or the most convenient temperature for mixing reactants.

Under these conditions, a nucleic acid replication or detection reaction is vulnerable to the generation of sideproducts when the primer or probe anneals to non-target sequences under permissive temperature and solvent conditions or when the signal-dependent catalyst operates even in the absence of target sequence; and the present invention reduces such side reactions by allowing reactant segregation before reaction and reactant mixing when the temperature has risen to stringent levels. In this case, one needs to formulate the wax or grease so that it does not melt at least until approximately stringent conditions have been reached. More generally, however, aspects of this invention may benefit any aqueous reaction where a vapor barrier is needed to minimize solvent or other reagent evaporation and where there are functional advantages to vapor barrier solidity at lower temperatures and fluidity at higher temperatures.

From the above description and the following examples, one of ordinary skill in the an can appreciate the many diverse aspects of the present invention as encompassed by the following claims.

EXAMPLE 1

Effect of MgCl$_2$ Segregation on PCR Reagent Storage Stability

Two mixtures ("pre-mixes") of PCR reagents were prepared in deionized water and stored frozen at −20° C. in 50 μl aliquots in 500 μl Eppendoff microfuge tubes. Premix A contained 0.055 enzyme unit/μl of *Thermus aquaticus* (Taq) DNA polymerase I cloned and expressed in *E. coli* (Ampli-Taq® from Perkin Elmer Cetus Instruments); 0.11 mM of each of the four common dNTPs (sodium salts from Pharmacia); 0.33 μM of each of two PCR primers designed to amplify a 239 or 242 nucleotide sequence of the HLA DQα gene (Saiki et 1989, *Proc. Natl. Acad. Sci. USA* 86:6230–6234); 22 mM Tris Cl, pH 8.3; and 110 mM KCl. Premix B contained the same components as Premix A but also contained 8.05 mM MgCl$_2$.

At various times over a five-day interval, four robes containing each of the premixes were thawed and placed in an airtight screw-capped plastic container at room temperature. At the end of this interval, the robes were treated in the following manner: (a) 50 μl of deionized water were added to each tube containing Premix B; (b) 50 μl of 8.05 mM MgCl$_2$ were added to each tube containing Premix A; (c) two drops of mineral oil (Sigma Chemical Co.) were added to each robe; and (d) 0.3 or 1.0 ng of purified human genomic DNA from the human cell line WT51 in 10 μl of deionized water was added to each tube.

The robes were capped and immediately placed in a Perkin Elmer Cetus Instruments Thermal Cycler programmed to run 32 cycles of the following sequence: 94° C. for 1 minute, 60° C. for 30 seconds, and 72° C. for 30 seconds with the fastest possible thermal stepping and a 7 minute extension of the last-cycle 72° C. incubation.

After this PCR amplification, the amplified DNA was analyzed by agarose gel electrophoresis at room temperature in a gel containing 3.0 g NuSieve® agarose and 1.0 g of SeaKem® agarose (FMC Corporation), and 100 ml of TBE buffer. TBE buffer contains 0.089M Tris borate, pH 8.3, and 0.025M Na$_2$ EDTA. The electrophoresis running buffer was TBE. The separation was run at 150 V, approximately 50 milliamperes, for 2 hours. Each gel sample slot contained 10 μl of PCR reaction mixture plus 2 μl of 25% Ficoll 400, 0.25% bromphenol blue, and 0.25% xylene cyanol. After electrophoresis, the gel was stained in 0.5 μg/ml ethidium bromide in TBE buffer for 15 minutes and destrained in H$_2$O for 15 minutes.

The ethidium-stained electrophoretic bands of DNA were visualized on a 300 nm ultraviolet transilluminator. The robes containing Premixes A and B had been subjected to four different incubation intervals at room temperature before running PCR: 1.5 hours, 6 hours, 1 day, and 5 days. All of the Premix A samples, except those incubated 1.5 hours at room temperature before adding 0.3 ng of human genomic DNA, showed the expected 240 base-pair PCR product band and only trace amounts of primer dimer. Only one of the Premix B samples, incubated 1.5 hours at room temperature before adding 1 ng of DNA, showed the 240 base-pair product. The Premix B samples showed increasing amounts of primer dimer and primer oligomers, directly related to the time the samples were incubated at room temperature before PCR. The data showed that even relatively short incubations of complete mixtures of PCR reagents at room temperature before running PCR inactivate them. This inactivation may be related to primer dimer accumulation. On the other hand, the PCR reagent subset lacking magnesium retained full activity after even five days at room temperature. The present example also shows the practicality of performing PCR when complementary reagent subsets are mixed just before amplification is started.

In other experiments designed and executed substantially as described above, Premix A (lacking magnesium) showed efficient and reproducible amplification of the 240 base-pair HLA DQα target from 0.3 ng and 1 ng of human genomic DNA and produced no or barely detectable primer dimer after 12 days storage at −20° C., 4° C., 25° C., and 37° C. whereas Premix B amplified the same amounts of target erratically and produced considerable amounts of primer dimer after 21 or 27 days storage at −20° C. These same experiments showed that vigorous mixing of Premix A with MgCl$_2$ shortly before amplification, rather than layering of reagent subsets, increased primer dimer yield and reduced specific product yield. In still other similar experiments, Premix A showed complete storage stability for 2 months at 45° C. Premix B failed to produce detectable amplified specific PCR product after several days at room temperature.

EXAMPLE 2

Effect of Completeness of MgCl$_2$ Segregation on PCR Specificity

All PCR reactions used Premix A as defined in Example 1, and the reaction mixes were adjusted to 8.05 mM MgCl$_2$ shortly before amplification. The tubes containing pre-mix were stored frozen until shortly before use. The test sample consisted of 0.1 ng/μl purified DNA from the RS-2 cell line; 10 μl of test sample and 50 μl of MgCl$_2$ were added to each reaction tube before carefully layering 50 μl of mineral oil on top. Six reaction tubes were set up under each of three conditions: (a) the pre-mix was cooled to 0° C. in an ice bucket; 50 μl of MgCl$_2$ was carefully layered on top; 10 μl of DNA was carefully layered on top of the MgCl$_2$; (b) layering was done as in (a), but the pre-mix was at 30° C.; and (c) the DNA was layered on top of the pre-mix at 30° C., followed by the MgCl$_2$.

Immediately after set-up, all tubes were transferred to a Perkin Elmer Cetus Instruments Thermal Cycler and subjected to the following program: 1 minute at 98° C., 30 seconds at 60° C., and 30 seconds at 72° C. for 2 cycles; 1 minute at 94° C., 30 seconds at 60° C., and 30 seconds at 72° C. for 35 cycles; and a final 10 minutes at 72° C. Agarose gel electrophoresis and ethidium staining were essentially as described in Example 1.

All reaction tubes showed the expected 240 base-pair HLA DQα product band, but layering condition (a) gave less product than condition (b) which gave less product than condition (c). Layering condition (a) gave more primer dimer than condition (b), which gave more primer dimer than condition (c). Most significantly, layering conditions (a) and (b) gave a second nonspecific product closer to primer dimer than to specific product in molecular weight, which was completely absent with layering condition (c). Similar experiments in which no DNA was added showed none of the second nonspecific product, suggesting that it results from mispriming of human genomic DNA rather than from primer oligomerization. As this mispriming reaction must occur before DNA denaturation during the first PCR cycle, its existence implies that the human genomic DNA of the test sample must be significantly single-stranded. When the electrophoretic mobility of this nonspecific product was compared to those of fragments from a HaeIII digest of φX174 RF DNA (size standards from Bethesda Research Laboratories), the nonspecific product was seen to be approximately 91 base pairs in size. Primer dimer was approximately 68 base pairs in size.

This experiment confirmed the value of segregating magnesium from the complementary PCR reagent subset until the actual start of PCR thermal cycling. Interposition of even just a 10 µl layer of PCR-reagent-free test sample between the two reagent subsets served to reduce primer dimer formation and prevent a mispriming-dependent amplification of nonspecific product Surprisingly, layering at 0° C. gave more primer dimer than layering at room temperature. Taq DNA polymerase I appears to catalyze primer dimer formation even at 0° C.

EXAMPLE 3

Effect of a Grease or Wax Vapor Barrier

PCR reagent Premix A and stock 8.05 mM MgCl$_2$ were prepared as described in Example 1. The human genomic DNA used as a test sample was purified from the cell line HL-60 and formulated in water at a concentration of 0.3 ng/µl. To PCR reaction tubes containing 50 µl of Premix A were added 40 mg masses of the following waxes or grease: Paraplast (Monoject Industries), 58°–60° C. melting paraffin (Aldrich Chemical Co.), octacosane (Aldrich Chemical Co.), Vaseline® Petroleum Jelly (Cheeseborough Ponds), Pentaerythritol tetrabehenate (Lipo Chemicals), and BeSquare 175 (Calwax Corporation). Several other reaction tubes containing 50 µl Premix A received 75 µl of light mineral oil (Sigma Chemical Co.). All tubes were capped and incubated in an 85° C. water bath for 90–120 seconds (until the wax melted into a layer over the premix), then cooled to room temperature.

On top of each wax, grease, or oil layer was added a mixture containing 50 µl of 8.05 mM MgCl$_2$ and 10 µl of 0.3 ng/µl purified human genomic DNA. The mixture added on top of oil instantly penetrated the oil to join the premix. All tubes were transferred to a Perkin Elmer Cetus Instruments Thermal Cycler already heated to 90° C. After 90 seconds at 90° C., 35 cycles were executed according to the following program: 30 seconds at 95° C., 30 seconds at 55° C., 30 seconds at 72° C., with a final 7 minute extension at 72° C. Thermal ramps between temperatures proceeded as rapidly as possible.

PCR product was analyzed by ethidium-stained agarose gel electrophoresis essentially as described in Example 1. All of the reactions with the wax and oil vapor barriers listed above gave the specific 240-base pair PCR product Paraplast, octacosane, and pentaerythritol tetrabehenate gave specific PCR product in comparable yield to mineral oil. Various waxes gave primer dimer in yields ranging from none to heavy, whereas mineral oil gave a small amount of primer alimet. Preliminary experiments of the same design with certain other waxes, such as eicosane (Aldrich Chemical Co.), tricosane (Aldrich Chemical Co.), tetracosane (Aldrich Chemical Co.), and carnauba wax (Calwax Corporation) gave no PCR product. However, later experiments showed that performance of wax layers in the mass range of 40–50 mg was erratic; sometimes the MgCl$_2$ and DNA mixture would easily fall through the melted wax and mix well with the premix but sometimes would not. Therefore, single successful or unsuccessful reactions with such large wax masses predicted neither reliable amplification nor uniform unsuitability. For example, later experiments showed that eicosane worked as well as Paraplast and paraffin, which gave yields of both specific product and primer primer comparable to those with a mineral oil vapor barrier. Cetyl palmitate (Serva Biochemicals) and Ultraflex (Calwax Corporation) also served as liquid barriers yielding useful amounts of specific product and only low amounts of primer filmer. Mineral oil was mixed with paraffin and with Paraplast at concentrations up to 25% (by mass) to give liquid barriers which gave specific amplification as good as mineral oil alone with lower yields of primer dimer. These mixtures gave no higher PCR specificity or yield than the waxes alone, but they were somewhat softer and easier to penetrate with sampler tips used to withdraw the PCR product for electrophorefic analysis.

EXAMPLE 4

Minimizing the Mass of a Wax Vapor Barrier

In Example 3 and related experiments, a 40 mg mass of wax was layered over 50 µl of Premix A; and a 60 µl mixture of MgCl$_2$ and DNA was placed above the wax was so that the final aqueous volume under the wax was 110 µl. Although these quantities led to complete coverage by the wax liquid barrier before thermal cycling and complete coverage by the wax vapor barrier during and after thermal cycling, the resulting wax layer was so thick that post-PCR penetration by a micropiper tip was inconvenient and required close control. The pressure on the micropiper needed to break through the wax often led to sudden penetration and spurting of PCR reaction mixture (including amplified nucleic acid) past the micropipet tip, potentially contaminating the laboratory environment with PCR product which could back-contaminate later amplifications.

Experiments to test the minimum mass of paraffin covering completely 100 µl of water showed that between 30 and 35 mg of wax were needed for complete coverage as a liquid barrier, although vapor barrier effectiveness (reduction of water evaporation) appeared to be complete between 25 and 30 mg. The PCR reaction tube was a standard uncoated 500 µl microcentrifuge tube manufactured by CoStar. These experiments did not require thermal cycling, but only visual examination of wax layers under low magnification to detect holes, followed by heating of the closed tubes to 99° C. for 10 minutes before measuring the mass of water condensed on the walls and in the cap of the tube. The structural requirement for so much wax derived from the fact that the wax, like mineral oil, formed a concave-downward meniscus with the aqueous compartment below it and a concave-upward meniscus with the air above it at the time that the layer was formed. Therefore, to get complete coverage at the center of the tube, a much thicker layer was needed at the wall of the tube. The focus of efforts to render the wax layer thin enough to be practical rested on compositions which reduced the depth of the menisci, creating a more uniform distribution of wax across the top of the aqueous compartment, in the thinnest layer giving complete coverage. Paraffin was the wax used in all of these efforts. Although other waxes must show the same semiquantitative behavior as paraffin, their quantitative requirements might differ somewhat.

Inclusion in the paraffin of 1% Brij 52 (diethyleneglycol monocetyl ether, Serva Fine Biochemicals), Brij 30 (triethyleneglycol monolauryl ether; Serva Fine Biochemicals), or polyoxyethylene-9-lauryl ether (Sigma Chemical Co.) reduced the minimal wax mass for complete coverage from between 30 and 35 mg to between 20 and 25 mg, but micropiper tip penetration was still difficult. Inclusion in the wax of 200–400 mesh polystyrene-divinylbenzene beads (BioBeads SM-X8, BioRad Laboratories) at mass percent of 10 or 20 reduced the minimum effective mass of wax to between 25 and 30 mg. More beneficially, micropiper tip penetration was effortless, and the wax broke away without clogging the sampler tip. Bead concentrations of 30%, and 40% did not give complete coverage at 30 mg of wax. Although 10%, 20%, or 40% (by mass) of Vaseline® Petroleum Jelly in paraffin was not tested for effect on the minimal mass of wax needed for complete coverage, at 40 mg of these mixtures (somewhat above the probable minimum), micropiper tip penetration was easy because the wax was somewhat softened. However, the wax tended to clog some sampler tips. Inclusion in a mere 10 mg of paraffin of a 3 mm diameter circle of polypropylene monofilament mesh (Propyltex™ silk screening fabric; Tetko Corporation) weighing approximately 0.5 mg gave complete coverage of 50 µl of water in an uncoated polypropylene microcentrifuge tube. Repeat of this experiment with 7 mg of wax did not quite give complete coverage. Although a somewhat larger mass of wax would be needed to cover the 100 µl of water used in the previous tests, that amount would not nearly approach the 30–35 mg needed in the absence of mesh or surfactant.

To test the effect of coating PCR reaction tubes with surfactant, 500 µl microcentrifuge tubes were incubated for 30 minutes at room temperature containing 5% solutions in 1-propanol of each one of six surfactants: polyoxyethylene-9-lauryl ether, Span 40 (sorbitan monopalmitate; Sigma Chemical Co.), Brij 30, Tween 85 (polyoxyethylene sorbitan trioleate; Sigma Chemical Co.), Span 80 (sorbitan monooleate; Sigma Chemical Co.), and Brij 52. After drainage of the surfactant solutions from the tubes, the tubes were air-dried. Various masses of paraffin (7.5, 11.3, 15, and 18.8 mg) were layered on top of 50 µl of 0.06M KCl in $H_2O$ in each tube. After the wax layers had hardened and were examined visually for holes under low magnification, they were covered with 50 µl of a 0.1% solution of methylene blue in $H_2O$. After the tubes were capped and stored for 3.5 days at room temperature, they were examined visually for signs of dye leakage from the upper aqueous layer into the lower one. Then they were immersed for two minutes in a 95°–97° C. water bath, allowed to air-cool to room temperature, and rechecked visually for signs of holes in wax covering the 100 µl of combined aqueous layers. During heating, they were observed for the timing and completeness of dye penetration of the melted wax and mixing with the lower aqueous layer.

Although two surfactants (Tween 85 and Span 80) gave greatly improved performance over a control tube which was uncoated, particularly in providing complete coverage of 50 µl of aqueous solution with only 15 mg of wax (no holes and no dye leakage after 3.5 days), only Tween 85 gave complete coverage of 100 µl. Two other surfactants (polyoxyethylene-9-lauryl ether and Brij 30) gave partial improvement over uncoated tubes; no holes were seen in wax covering 50 µl, and dye penetration before heating did not occur immediately, but required several days of incubation. In this test, Span 80 was judged questionable on a different ground; it was the only coating which appeared to impede penetration and mixing of the upper aqueous layer upon heating to 95°–97° C. Therefore, Tween 85 provided special benefit in comparison to the other surfactants tested or to no coating, greatly reducing the mass of paraffin needed for complete coverage of 100 µl of water from between 30 and 35 mg to approximately 15 mg. Furthermore, the 15 mg layer of wax covering an 100 µl aqueous compartment was very easily penetrated by a micropipet tip. However, it is expected that other surfactants not yet tested will meet or surpass this performance, as those tested represent only a small fraction of the hundreds available commercially.

In a further test of Tween 85-coated reaction tubes, 7.5 mg, 11.3 mg, and 15 mg paraffin layers containing 0%, 0.34%, and 1.2% of Tween 85 were used in an experiment just like the surfactant coating screen just described. This time the mass of water distilled onto the upper walls and cap of the tubes during 10 minutes at 99° C. was measured. This last criterion showed a marked benefit from either Tween 85 concentration in the wax (Tween 85 also coating the tubes). Surfactant also helped to achieve complete coverage of 50 µl of aqueous solution with only 7.5 mg of wax, but did not allow complete coverage of 100 µl with either 11.3 mg or 7.5 mg.

Still further tests of Tween 85, using a similar experimental design, showed that 1% Tween 85 in 56°–61° C. melting paraffin worked approximately equally well in Tween 85-coated and uncoated robes. However, this test did not include storage for several days or actual PCR amplification. Both conditions gave better coverage than the use of Tween-85-coated tubes without Tween 85 in the wax, and much better coverage than the use of untreated tubes without Tween 85 in the wax. According to the dual criteria of easy micropipet penetration and complete coverage (no holes in the wax and minimal evaporation of water from reaction mixture during thermal cycling), the following wax masses were found to be preferred for the associated underlying water volumes when paraffin contained 1% Tween 85:8 mg with 25 µl water, 12 mg with 50 µl, 16 mg with 75 µl, 18 mg with 100 µl, 22 mg with 150 µl, and 26 mg with 200 µl. These masses are several mg higher than the minimum effective masses, but help to assure that all tubes will perform well, as there is certain to be some randomness in both the mass of wax delivered and the resulting performance.

EXAMPLE 5

Effect of Improved Wax on PCR Amplification

Tween 85 was dissolved in 1-propanol to a concentration of 1% by mass. Approximately 0.5 ml aliquots of this Tween 85-propanol solution were added to 500 µl microcentrifuge tubes and incubated at room temperature for about 30 minutes before draining the tubes with a glass Pasteur pipet. The tubes were dried under vacuum (22 inches Hg) at room temperature for 30 minutes. Tween 85 was dissolved at 70°–90° C. in 56°–61° C. melting paraffin (Aldrich Chemical Co.) to a concentration of 1%. Fourteen mg aliquots of 1% Tween 85 in paraffin were delivered with an SMI Micro/Pettor from 70°–90° C. melted wax onto a polyethylene weighing boat sitting on ice. The individual 14 mg pellets of hardened wax were delivered individually to separate Tween 85 coated reaction tubes. Fifty µl aliquots of Premix A (Example 1) were added to the wax-containing tubes, which were incubated approximately 2 minutes at 70°–80° C. and allowed to air-cool to room temperature. All wax layers were free of holes. On top of them were added 60 µl of mixture of 6.71 mM $MgCl_2$ and enough purified human genomic DNA to contain 30 genomic copies (0.1 ng).

These completed reaction tubes were subjected to the following amplification program in a Perkin Elmer Ceres Instruments Thermal Cycler: two cycles of 1 minute at 98° C., 30 seconds at 60° C., and 30 seconds at 72° C.; 35 cycles of 1 minute at 94° C., 30 seconds at 60° C. and 30 seconds at 72° C., followed by a 10 minute incubation at 72° C. All thermal ramps between temperatures were performed as rapidly as possible. Ethidium-stained gel electrophoresis was performed essentially as in Example 1. Sixteen replicate reactions were run as just described. Another six tubes contained mineral oil instead of wax; in them the 60 µl of DNA and $MgCl_2$ mixed immediately with the 50 µl of Premix A upon addition to the tubes. One more control tube used wax with no added DNA and one used oH with no added DNA. Gel electrophoresis showed that fifteen of the sixteen wax-covered amplifications generated the expected 240 base-pair specific PCR product and significant amounts of primer dimer. Three of the fifteen showed significantly less of the specific product than did the others. All six oil controls showed somewhat but not greatly higher yields of specific product than did the successful wax-covered amplifications, but they also showed the 91 base-pair mix-primed nonspecific product described in Example 2, completely absent when wax was used. Omission of test sample DNA resulted in a normal yield of primer dimer and no detectable 240 base-pair or 91 base-pair product. Wax gave somewhat larger primer dimer than did oil, and somewhat higher yields of primer dimer than did oil.

This experiment showed acceptably reproducible PCR amplification when 14 mg of paraffin containing 1% Tween 85 replaces 100 µl (approximately 80 mg) of mineral oil and serves to segregate $MgCl_2$ and test sample from the remaining PCR reagents until the first amplification cycle. This amplification was significantly more sensitive than those in Examples 1–3, which started with at least 100 genomic copies of HLA DQα DNA.

Similar experiments in which the mass of wax was doubled from 14 to 28 mg showed much reduced yields of specific product and almost normal yields of primer dimer. Similar experiments (with 14 mg of wax) in which test sample was added to premix before wax layering and only $MgCl_2$ was placed above the wax seemed to give somewhat higher and more reproducible yields of specific product and lower yields of primer dimer probably because the test sample spent more time at high temperature during the first one or two cycles. Similar experiments in which the 60 µl of test sample and $MgCl_2$ were placed below the wax and the 50 µl of premix were placed above also appeared to give higher and more reproducible specific product yields and reduced primer alimet yields. These last reactions also gave a more complicated and variable primer dimer pattern, more like that seen with oil vapor barriers. These variations on the normal way of using Tween 85-containing wax to segregate $MgCl_2$ and test sample from the other PCR reagents in Tween 80 coated tubes suggest that additional improvements may result from further reduction in the wax mass and by lowering the wax melting point so that the reactants mix more rapidly after the first thermal cycle is started. These changes and other simple ones, such as prolonging the duration of the rust-cycle denaturation segment (currently 1 minute at 98° C.) can be used to improve first-cycle DNA denaturation and thereby increase yield.

We claim:

1. A sealed container containing an aqueous solution comprising a thermostable DNA polymerase and a polymerase chain reaction (PCR) primer pair said pair flanking a predetermined nucleic acid sequence to be amplified by PCR wherein the magnesium concentration of the solution is less than about $10^{-4}$M.

2. The container of claim 1 further comprising an aqueous suspension or solution of a magnesium compound, wherein said magnesium-containing suspension or solution is present as a separate first layer substantially unmixed with a second layer comprising the aqueous solution comprising the thermostable DNA polymerase and the polymerase chain reaction (PCR) primer pair.

3. The container of claim 2 also comprising a test sample containing nucleic acid.

4. The container of claim 2 wherein the two layers containing, separately, the magnesium compound and the aqueous solution comprising a thermostable DNA polymerase and a polymerase chain reaction (PCR) primer pair, are separated by a third aqueous layer containing no PCR reagents, wherein all three layers are substantially unmixed with one another.

5. The container of claim 2 wherein the two layers differ in density by at least about 0.2 g/ml, and the upper layer is the denser of the two.

6. The container of claim 4, wherein the three layers differ in density from one another by at least about 0.2 g/ml, the upper layer is the most dense, and the lower layer is the least dense.

7. A container of claim 1 wherein the container is molded to match wells in a thermal cycler.

8. A method of inhibiting dimerization of polymerase chain reaction (PCR) primer pairs in a PCR reaction mixture for amplifying a target nucleic acid where said PCR reaction mixture comprises at least a thermal stable DNA polymerase and a PCR primer pair said method comprising:

(a) mixing a thermostable DNA polymerase and a PCR primer pair in an aqueous solution having a magnesium concentration of less than about $10^{-4}$M said mixture in a container;

(b) storing the solution of step (a) for more than 5 days prior to step (c);

(c) adding magnesium to the aqueous solution in an amount sufficient to induce polymerase activity;

(d) adding deoxynucleoside triphosphates to the reaction aqueous solution;

(e) adding target nucleic acid; and (f) thermal cycling the aqueous solution to amplify the target nucleic acid.

9. A method of claim 8 wherein the magnesium of step (c) is stored in the container and is physically separate from the aqueous solution containing the polymerase.

10. A method of claim 8 wherein the aqueous solution of step (a) is stored at room temperature.

11. A polymerase chain reaction (PCR) kit comprising a sealed and sterile container containing an aqueous mixture containing PCR reagents, said reagents comprising a thermostable DNA polymerase and a PCR primer pair said pair flanking a predetermined sequence to be amplified by PCR wherein said mixture has a magnesium concentration of less than about $10^{-4}$M and instructions for how to use said container.

12. A kit of claim 11 wherein the container further contains magnesium ions placed behind a barrier situated between the magnesium ions and the aqueous mixture containing PCR reagents wherein the barrier releases said magnesium upon thermal cycling.

13. A kit of claim 11 further comprising a second container containing a magnesium salt.

14. An aqueous solution comprising a thermostable polymerase and a PCR primer pair wherein the solution is contained within a container that is closed to the atmosphere and the solution has a magnesium concentration of less than $10^{-4}$M.

15. An aqueous solution of claim 14 which further comprises deoxynucleoside triphosphates.

16. A container of claim 1 wherein the solution is sterile.

17. A solution of claim 14 wherein the solution is sterile.

18. A sterile aqueous solution comprising a thermostable polymerase and a PCR primer pair wherein the solution is contained within a container that is closed to the atmosphere and the solution has no added magnesium.

* * * * *